United States Patent [19]

Yang et al.

[11] Patent Number: 4,927,018
[45] Date of Patent: May 22, 1990

[54] DISPOSABLE COVERED NEEDLE SAFETY ASSEMBLY

[76] Inventors: Herbert Yang; Patrick Han; Frank Yu, all of 6-1 Fl., No. 185, Yungchi Road, Taipei, Taiwan

[21] Appl. No.: 280,322

[22] Filed: Dec. 6, 1988

[51] Int. Cl.⁵ .................. B65D 83/10; A61M 5/00
[52] U.S. Cl. .................... 206/365; 206/363; 206/364; 604/110; 604/198; 604/263
[58] Field of Search ............ 206/363, 364, 365, 367, 206/368; 604/110, 198, 263

[56] References Cited

U.S. PATENT DOCUMENTS

| | | | |
|---|---|---|---|
| 4,573,976 | 3/1986 | Sampson et al. | 604/263 |
| 4,693,708 | 9/1987 | Wanderer et al. | 604/263 |
| 4,702,738 | 10/1987 | Spencer | 604/263 |
| 4,772,272 | 9/1988 | McFarland | 604/263 |
| 4,801,295 | 1/1989 | Spencer | 604/263 |
| 4,810,248 | 3/1989 | Masters et al. | 604/263 |
| 4,816,022 | 3/1989 | Poncy | 604/198 |
| 4,826,490 | 5/1989 | Byrne et al. | 206/365 |
| 4,840,185 | 6/1989 | Hernandez | 604/198 |
| 4,840,619 | 6/1989 | Hughes | 604/198 |
| 4,842,587 | 6/1989 | Poncy | 604/198 |

FOREIGN PATENT DOCUMENTS 2202748 10/1988 United Kingdom .............. 604/198

*Primary Examiner*—Stephen Marcus
*Assistant Examiner*—David Jenny
*Attorney, Agent, or Firm*—Fish & Richardson

[57] ABSTRACT

A needle assembly and cylindrical cover housing which are usable with a conventional hypodermic syringe. The needle assembly has a circular mount on it with catch slots and slanted surfaces. The cover housing has inward projections which are flexible so that the hypodermic syringe can be received in the cover housing and also for frictionally engaging in the catch slots so as to secure the needle assembly completely in the cover housing after usage.

1 Claim, 4 Drawing Sheets

DISPOSABLE COVERED NEEDLE SAFETY ASSEMBLY

BACKGROUND OF THE INVENTION

This invention relates to disposable injection devices, and in particular relates to a disposable covered needle assembly which before and after use, completely covers the needle so as to protect all concerned individuals therefrom.

In the past, disposable shots have been available, but none have adequately provided for protection of the person administering the injection, the patient, and those handling waste materials. Most disposable shots have provided a plastic needle cover for protecting concerned individuals before usage of the shot. However, once the injection had been administered, often the needle was left exposed, thereby posing a pricking hazard and hazard of infection. Even if the person administering the shot replaced the needle cover after use, there was always the slight possibility that that person could actually stick himself with the needle while replacing the needle cover.

It is the purpose of this present invention, therefore, to mitigate and/or obviate the abovementioned drawbacks in the manner set forth in the detailed description of the preferred embodiment.

SUMMARY OF THE INVENTION

A primary objective of this invention is to provide a disposable covered needle assembly and cover housing which eliminates the danger of exposed needles, before or after usage thereof.

Another objective of this invention is to provide such a disposable covered needle assembly and cover housing which can be used in conjunction with standard sized hypodermic syringes.

Further objectives and advantages of the present invention will become apparent as the following description proceeds, and the features of novelty which characterize the invention are pointed out with particularity in the claims annexed to and forming a part of this application.

DETAILED DESCRIPTION OF THE PREFERRED EMBODIMENT

Figure 1:
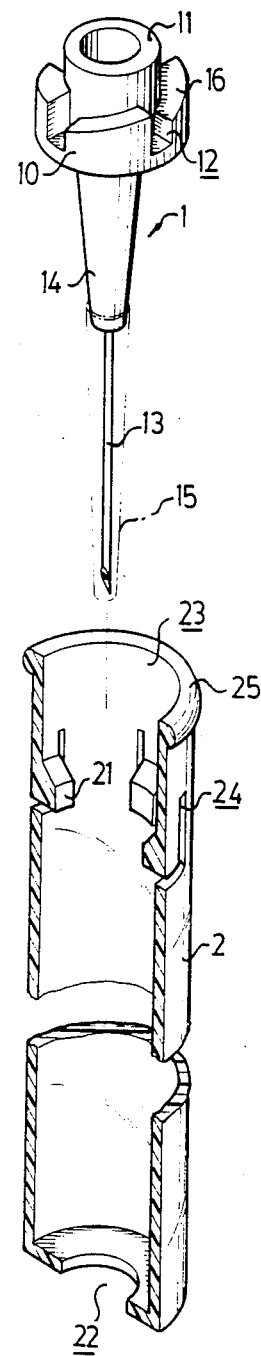
FIG. 1 is a perspective view of a disposable covered needle assembly and cover housing in accordance with the present invention with the cover housing partially cutaway.

Referring to FIGS. 1–4, it can be seen that the present invention comprises a disposable covered needle assembly 1 and cover housing 2 for use in conjunction with conventional hypodermic syringes 3.

The needle assembly 1 includes: a circular mount 10, an orifice 11, a conical end 14 and of course a needle 13. The circular mount 10 protrudes from an outer surface of the needle assembly 1 proximate to the orifice. The catch slots 12 are vertically oriented on an upper portion of the circular mount 10 with slanted surfaces 16 therebetween. The slanted surfaces 16 all slant in the same radial direction, that is, either counter clockwise (CCW) or clockwise (CW). The orifice 11 is inwardly tapered to frictionally engage with a discharge nozzle 33 of the hypodermic syringe 3. A needle 13 is set on the end of the needle assembly opposite to the orifice 11 with a needle cover 15 thereon as an added safety feature, as will be explained in more detail later in the specification.

The cylindrical cover housing 2 slidably and frictionally encompasses the hypodermic syringe 3. The cover housing 2 has inward projections 21 on the inner surface thereof proximate to the main opening 23. The main opening 23 has a lip 25 therearound for structural soundness and also to act as a grip for the cover housing 2. The inward projections 21 also have a U-shaped slot 24 therearound so as to be outwardly flexible when the hypodermic syringe 3 is inserted into or retracted from the cover housing 2. The cover housing 2 has a circular aperture 22 at an end opposite the inward projections 21 for allowing the lower portion of the needle assembly 1 to pass therethrough. When the lower portion of the needle assembly 1 projects outward from the aperture 22 the needle cover 15 still covers the needle 13 until removed by the person administering the shot. This is an added safety feature preventing any accidental pricking during projecion of the needle 13. The cover housing 2 is preferably made of a clear plastic material, such as polystyrene, polycarbonate or the like.

The inward projection 21 has a slanted surface at the upper end thereof to facilitate sliding of the cover housing 2 therealong when the user pulls the cover housing 2 towards the stop 31 of the syringe 3. The lower end of the inward projection 21 is rectangular and square (perpendicular) with respect to the wall of the cover housing 2 (see FIG. 1).

Figure 2:
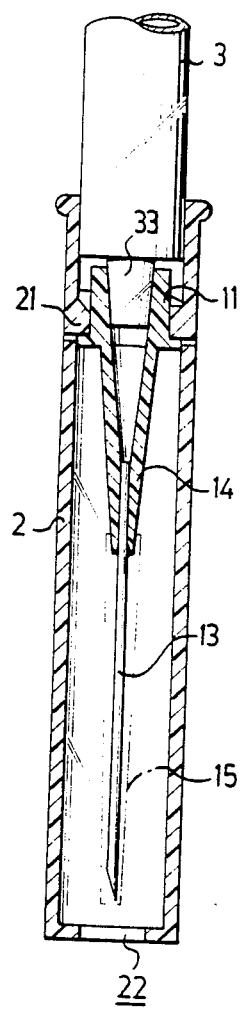
FIG. 2 is an elevational view of the disposable covered needle assembly and cover housing of FIG. 1 before usage thereof.
Figure 3:
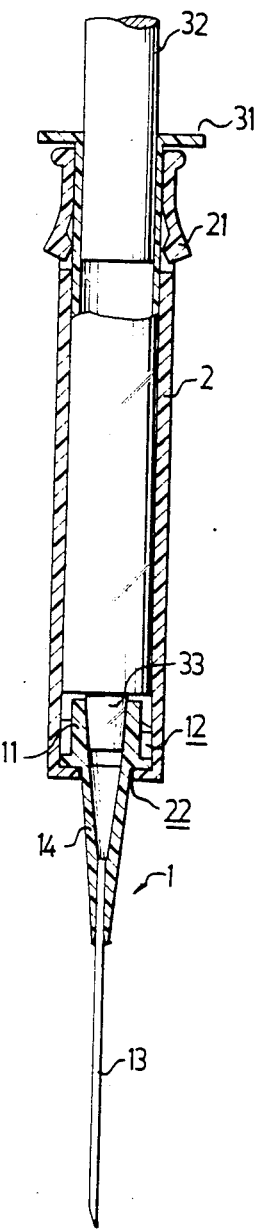
FIG. 3 is an elevational view of the disposable covered needle assembly and cover housing of FIG. 1 with the needle assembly in projected position with the needle cover removed.
Figure 3:
Figure 4:
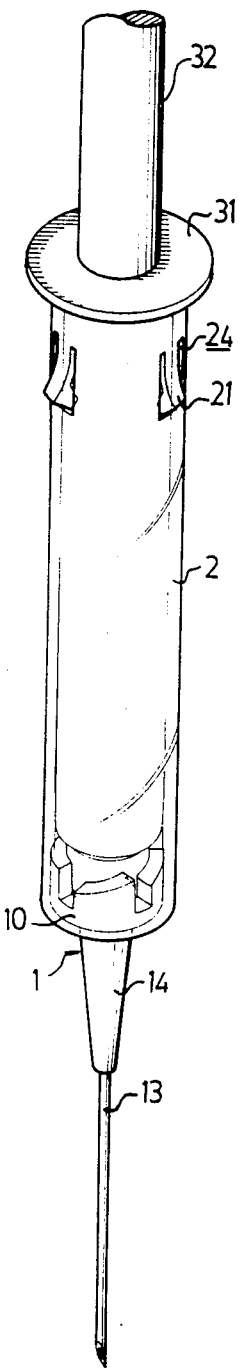
FIG. 4 is a perspective view of the disposable covered needle assembly and cover housing of FIG. 1 in conjunction with a conventional hypodermic syringe with the needle assembly in projected position with the needle cover removed.

The inward projections 21 frictionally fit into the catch slots 12 before the disposable covered needle assembly 1 is used. A lower portion of the needle assembly 1 is projectable from the circular aperture 22 by pulling the lip 25 towards the stop 31 on the end of the hypodermic syringe 3. The lower portion of the needle assembly 1 is retractable from the circular aperture 22 by pulling the cover housing 2 away from the stop 31 so that the inward projections 21 flex inwards to be turnable on the slanted surface 16 and to frictionally engage with the catch slots 12 and to totally enclose the needle assembly 1 inside of the cover housing 2 for waste disposal after use on a patient. Of course, if the syringe 3 is used to take a blood sample or the like, it should be retained after the cover housing 2 is disposed of. It is notable that when the needle assembly 1 is engaged with the inward projections 21, the orifice 11 is slightly lower than the lip 25 of the cover housing 2, as seen in FIG. 2. This arrangement prevents any incidental contact of the orifice which might cause the needle assembly 1 to be dislodged from the cover housing 2.

The catch slots 12 not only allow the inward projections 21 to frictionally fit into and engage therewith, but also allow the user to turn the needle assembly 1 while holding the cover housing 2 for easy removal of the entire assembly from the hypodermic syringe 3.

As various possible embodiments might be made of the above invention without departing from the scope of the invention, it is to be understood that all matter herein described or shown in the accompanying drawings is to be interpreted as illustrative and not in a limiting sense. Thus it will be appreciated that the drawings are exemplary of a preferred embodiment of the invention.

I claim:

1. A disposable covered needle assembly and cover housing for use in conjunction with conventional hypodermic syringes, wherein:

said needle assembly includes: a circular mount, an orifice, a conical end and a needle, said circular mount protruding from an outer surface of the needle assembly proximate to the orifice, catch slots being vertically oriented on an upper portion of said circular mount with slanted surfaces therebetween, said slanted surfaces all slanting in a same radial direction, said orifice being inwardly tapered to frictionally engage with a discharge nozzle of said hypodermic syringe, a needle being set on an end opposite to said orifice with a needle cover thereon;

said cylindrical cover housing slidably and frictionally encompasses said hypodermic syringe, said cover housing having inward projections on an inner surface thereof proximate to said main opening, said main opening has a lip therearound to act as a grip for said cover housing, said inward projections also having a U-shaped slot therearound so as to be outwardly flexible when said hypodermic syringe is inserted into or retracted from said cover housing, said cover housing having a circular aperture at an end opposite said inward projections for allowing a lower portion of said needle assembly to pass therethrough;

said inward projections frictionally fit into said catch slots before said disposable covered needle assembly is used, a lower portion of said needle assembly being projectable from said circular aperture by pulling said lip towards a stop on an end of said hypodermic syringe, said lower portion of said needle assembly being retractable from said circular aperture by pulling said cover housing away from said stop so that said inward projections flex to be turnable on said slanted surface and to frictionally engage with said catch slots and to totally enclose said needle assembly inside of said cover housing for waste disposal after use on a patient.

* * * * *